United States Patent [19]

Yagi et al.

[11] Patent Number: 5,091,400
[45] Date of Patent: Feb. 25, 1992

[54] CLATHRATE COMPOUND

[75] Inventors: Minoru Yagi, Kanagawa; Fumio Toda, Onsen, both of Japan

[73] Assignee: Kurita Water Industries Ltd., Tokyo, Japan

[21] Appl. No.: 563,945

[22] Filed: Aug. 7, 1990

Related U.S. Application Data

[63] Continuation of Ser. No. 453,943, Dec. 20, 1989, abandoned.

[30] Foreign Application Priority Data

Dec. 28, 1988 [JP] Japan .................. 63-334259

[51] Int. Cl.$^5$ ...................... A01N 31/04; A01N 43/80
[52] U.S. Cl. ..................... 514/372; 514/726
[58] Field of Search ................ 514/372, 726

[56] References Cited

U.S. PATENT DOCUMENTS 4,996,220 2/1991 Sekikawa et al. .................. 514/372

OTHER PUBLICATIONS

Neugebauer et al., J. Organometallic Chem., vol. 228(2), pp. 107-118 (1982).
Gilman, J.A.C.S., vol. 77, pp. 6380-6381 (1955).

Primary Examiner—Allen J. Robinson
Attorney, Agent, or Firm—Kanesaka and Takeuchi

[57] ABSTRACT 2,2'-Bis(α-hydroxydiphenylemthyl)biphenyl of formula:

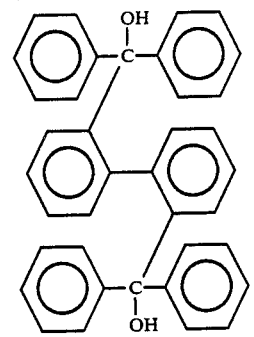

Clathrate compound is composed of the above compound as the host compound and a microbicide, 5-chloro-2-methyl-4-isothiazolin-3-one as the guest compound. The compound is formed such that, where diphenic acid is reacted with an alcohol for diesterification and then reacted with a Grignard reagent comprising a phenylmagnesium halide.

2 Claims, 2 Drawing Sheets

CLATHRATE COMPOUND

FIELD OF THE INVENTION AND RELATED ART STATEMENT

The present invention relates to a clathrate compound formed of 2,2'-bis(α-hydroxydiphenylmethyl)biphenyl, and a microbicide.

In a water system such as a cooling water system in various factory plants or a pulp and paper industry, slime of various bacteria, fungi, animals or vegetables adheres to the ducts or lines to cause various troubles.

Hitherto, for the purpose of preventing the troubles by slime or the like in such system, a microbicide (slime-controlling agent) has generally been employed as it may easily be handled and it is relatively low-priced. For instance, 5-chloro-2-methyl-4-isothiazolin-3-one of the following formula (II) (hereinafter referred to as "Cl-MIT") is widely used as a slime-controlling agent, a bactericide, an algicide or a fungicide for various water systems such as a cooling water system, a papermaking process system or a swimming pool, as it has an excellent microbicidal activity.

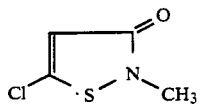
(II)

In general, Cl-MIT of the formula (II) is produced by a method where:
(1) a β-thioketoamide is halogenated in an inert organic ester solvent such as an acetate ester; or
(2) a β-substituted thiocyanoacrylamide or thiosulfatoacrylamide is treated with an acid to give an isothiazolone and this is further halogenated (Japanese Patent Publication No. 46-21240).

However, by anyone of the above-mentioned methods (1) and (2), it is impossible to selectively obtain only Cl-MIT but it is almost inevitable to produce 2-methyl-4-isothiazolin-3-one of the following formula (III) (hereinafter referred to as "MIT") as a by-product. The microbicidal capacity of the by-product MIT is approximately 1/10 time of Cl-MIT.

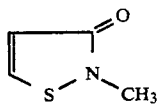
(III)

Moreover, it is impossible to selectively isolate only Cl-MIT from the reaction product mixture (containing the by-product MIT) by the related prior art technique. Under the situation, the mixture comprising Cl-MIT and the by-product MIT which has a low microbicidal capacity is unwillingly employed for the purpose.

On the other hand, Cl-MIT is extremely stimulative to the skin and a careful caution is necessary for handling the same, though it has an excellent microbicidal capacity in some degree. In addition, when Cl-MIT is put in water, it reacts with the organic substances (amines, reducing substances, etc.) in water to become inactive. Therefore, Cl-MIT could hardly maintain the microbicidal activity in water for a long period of time. Furthermore, since Cl-MIT is easily soluble in water, it would rapidly dissolve out into water when it is incorporated into a slime-controlling coating composition and the composition is coated on the inner walls of water ducts or lines. Accordingly, there is still another problem that the slime-controlling effect of Cl-MIT could not be maintained for a long period of time.

Accordingly, the water-soluble microbicidal agent which has heretofore been generally employed as a slime-controlling agent have various drawbacks with respect to the handling condition and the durability of the microbicidal activity, as it is toxic, the microbicidal activity thereof easily lowers and the water-solubility thereof is high.

The same shall apply to insecticides and perfumes. For instance, a natural essential oil such as 1,8-cineole (hereinafter referred to as "cineole") can be used as a perfume, a bactericide or a fungicide. However, most natural essential oils are highly volatile and it was difficult to maintain the effect thereof for a long period of time. Under the situation, development of slow-release insecticides or slow-release perfumes, namely fragrant agents which may maintain the insecticidal effect and the perfume for a long period of time and which can easily be handled is desired.

OBJECT AND SUMMARY OF THE INVENTION

The object of the present invention is to provide a new compound which is useful as a host compound for preparing clathrate compounds employable for providing excellent slow-release microbicides, low-release insecticides or slow-release perfume which are free from the above-mentioned problems, as well as to provide a method for preparing such a new compound.

Another object of the present invention is to provide a host compound for preparing clathrate compounds, which comprises the new compound.

Still another object of the present invention is to provide clathrate compounds with the host compound, which are industrially extremely useful.

As the first embodiment of the present invention, there is provided a new compound of 2,2'-bis(α-hydroxydiphenylmethyl)biphenyl (hereinafter referred to as "(HDPM)$_2$BP") of the following formula (I):

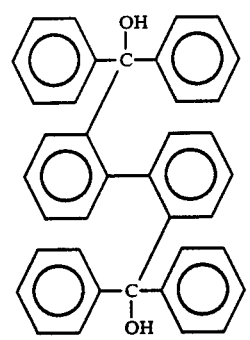
(I)

As the second embodiment of the present invention, there is provided a host compound for producing clathrate compounds, which comprises (HDPM)$_2$BP of the above-mentioned formula (I).

As the third embodiment of the present invention, there is provided a method for preparing (HDPM)$_2$BP where a diphenic acid is reacted with an alcohol for diesterification and the resulting diester is reacted with a Grignard reagent comprising a phenylmagnesium halide.

As the fourth embodiment of the present invention, there is provided a clathrate compound which comprises (HDPM)$_2$BP of the formula (I) as a host compound and a microbicide or a perfume as a guest compound.

(HDPM)$_2$BP of the present invention is a new compound which has a function as a host molecule for a microbicidal component such as Cl-MIT.

The clathrate compound prepared by applying a microbicidal component to the new compound may be in the form of a solid. Accordingly, where the clathrate compound is put in water, the microbicidal component may gradually dissolve out from the clathrate compound into water so that the microbicidal activity of the compound may be maintained for an extremely long period of time. In addition, as the microbicide is formed in the form of the clathrate compound, the toxicity of the microbicidal component as well as the stimulation thereof to the skin may be reduced. Moreover, the microbicidal component in the form of the clathrate compound does not react with any other substance during use thereof so that the microbicidal activity thereof is not lowered.

Accordingly, the thus obtained microbicidal component-containing clathrate compound can effectively be utilized as a slow-release microbicidal agent which may maintain the microbicidal activity for an extremely long period of time.

On the other hand, a perfume such as a natural essential oil can be formed into a clathrate compound with (HDPM)$_2$BP, which is also in the form of a solid. Accordingly, the natural essential oil-containing clathrate compound of the present invention is free from the drawback of the liquid oil itself, which will spread over when the oil-containing container falls down, and therefore it may easily be handled.

In addition, (HDPM)$_2$BP can also be employed for forming a clathrate compound containing a perfume component or insecticidal component. The resulting clathrate compound may gradually release the perfume component or insecticidal component therefrom with a lowered evaporation speed. Accordingly, the durability of the fragrant component and the insecticidal component may be elevated. By varying the grain size of the clathrate compound grains, the contact surface area of the grains with air may be controlled. Accordingly, the evaporation speed of the fragrant component and the insecticidal components from the clathrate compound grains may properly be adjusted. Moreover, the clathrate compound may be shaped into various forms.

In addition, (HDPM)$_2$BP of the present invention is also helpful for converting water-soluble microbicides or natural essential oils into powders, or for stabilizing or concentrating the same. Further, the property of (HDPM)$_2$BP as a host compound which may specifically select the guest compound to form a clathrate compound may be utilized for separation or isolation of the guest compound of a water-soluble microbicide or the like.

DESCRIPTION OF THE PREFERRED EMBODIMENTS

Next, the present invention will be explained in detail hereunder.

Figure 1:
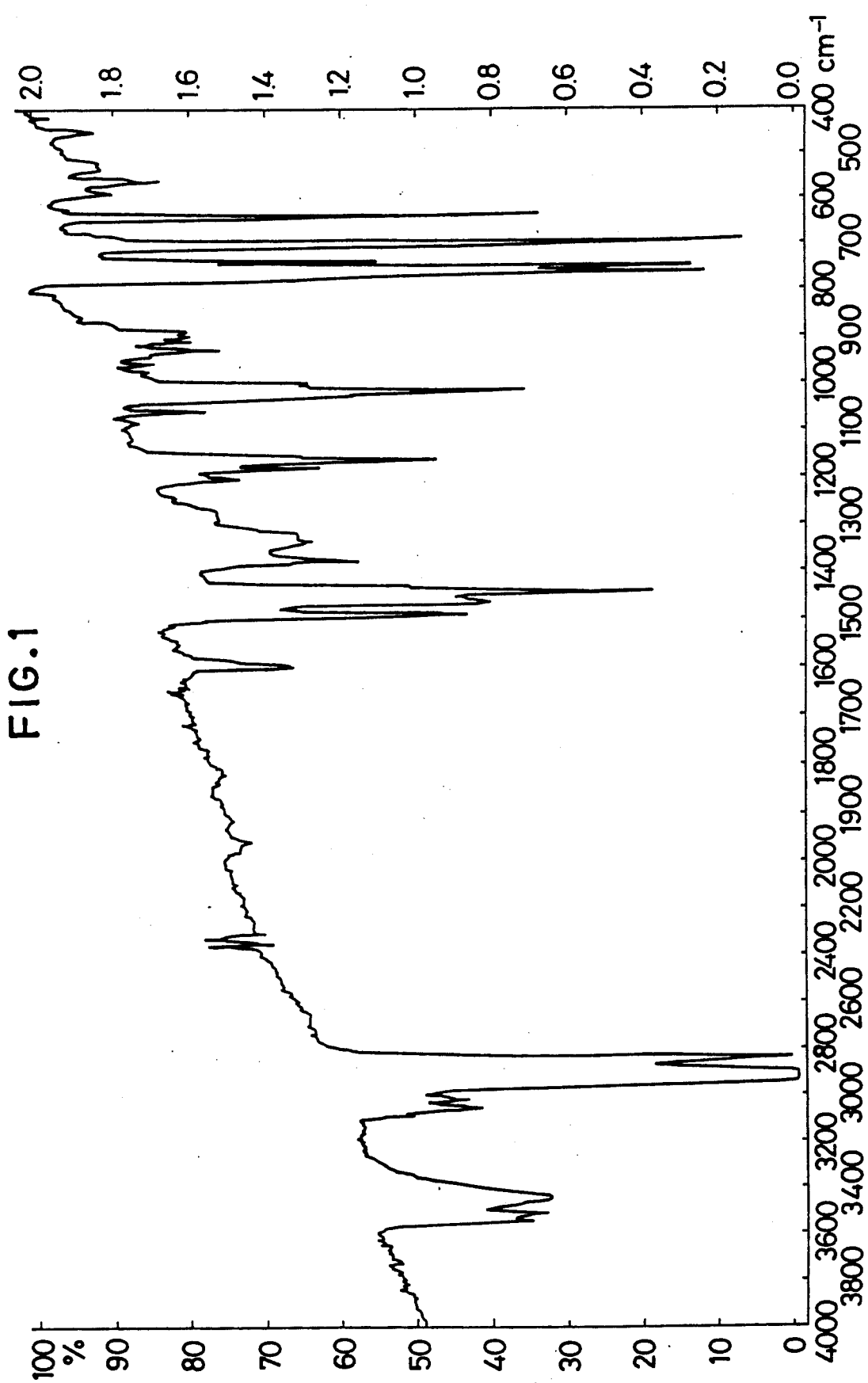
FIG. 1 is a drawing to show the IR spectrum of (HDPM)$_2$BP.
Figure 2:
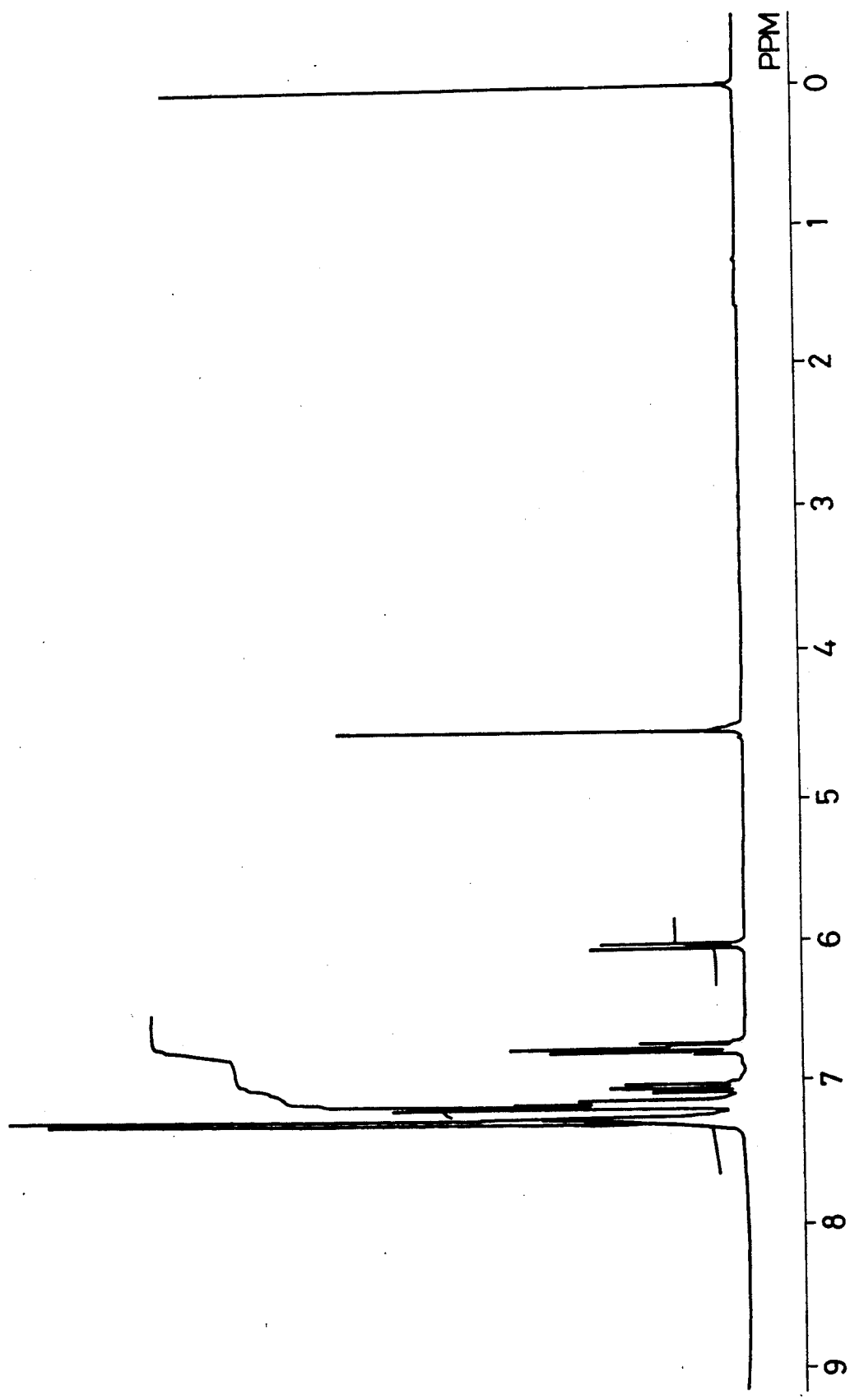
FIG. 2 is a drawing to show the NMR spectrum thereof.

(HDPM)$_2$BP of the formula (I) of the present invention is a new compound, having an IR spectrum as shown in FIG. 1 and an NMR spectrum as shown in FIG. 2.

The compound of the present invention can easily be prepared in accordance with the method of the present invention, for example, by the method mentioned below.

(1) A diphenic acid is dissolved in an alcohol such as methyl alcohol or ethyl alcohol, and an HCl gas is introduced into the resulting solution until saturation for completing the diesterification to produce a diphenic acid diester such as dimethyl diphenate or diethyl diphenate (Reaction Formula (1) below).

(2) A Grignard reagent comprising a phenylmagnesium halide such as phenylmagnesium bromide is produced, and this is reacted with the diphenic acid diester produced in (1) (Grignard reaction) to obtain (HDPM)$_2$BP as a crude crystal. For purifying the crude product, it may be recrystallized from benzene/n-hexane. Accordingly, a clathrate compound comprising (HDPM)$_2$BP and benzene is obtained, and the benzene is removed therefrom at 120° to 140° C. under reduced pressure whereby (HDPM)$_2$BP is obtained (Reaction Formula (2) below).

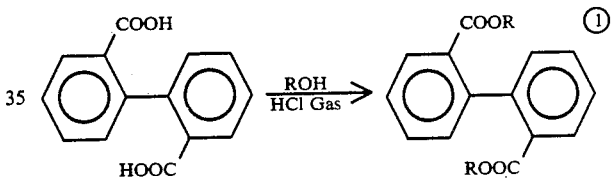

(In the formula, R represents an alkyl group such as methyl or ethyl group.)

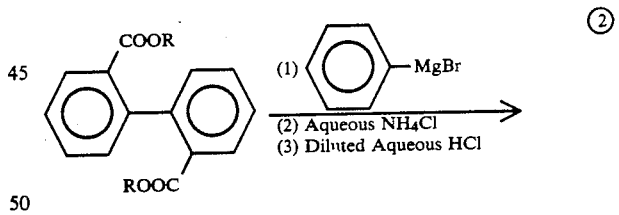

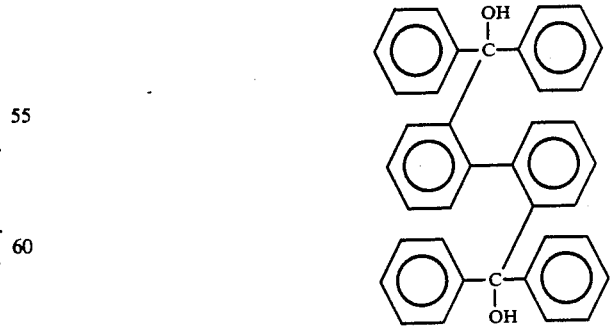

Examples of producing (HDPM)$_2$BP are mentioned below.

(HDPM)$_2$BP is useful as a host compound, which may be combined with a guest compound such as various anti-bacterial agents, microbicides or perfumes to give a stable clathrate compound.

The method for producing the clathrate compound of the present invention which contains (HDPM)$_2$BP of the present invention is not specifically limited. For example, a microbicide-(HDPM)$_2$BP clathrate compound can be prepared by the method (a) mentioned below.

(a) A microbicide-containing solution and (HDPM)$_2$BP are dissolved under heat in a solvent such as chloroform, whereupon the heating temperature is generally from 40° to 80° C., preferably from 50° to 60° C., and thereafter the resulting solution is allowed to stand as it is. The crystal precipitated is separated by filtration to obtain the intended clathrate compound. For instance, from a solution containing Cl-MIT and MIT and (HDPM)$_2$BP, Cl-MIT-(HDPM)$_2$BP clathrate compound can selectively be formed.

On the other hand, a clathrate compound comprising a perfume such as cineole and (HDPM)$_2$BP may be prepared by the following method (b) or (c).

(b) (HDPM)$_2$BP is dissolved in a perfume under heat, whereupon the heating temperature is generally from 100° to 120° C. (liquid-liquid reaction), and thereafter the resulting solution is allowed to stand as it is. The crystal precipitated is separated by filtration to obtain the intended clathrate compound.

(c) (HDPM)$_2$BP and a perfume are merely blended (solid-liquid reaction). The solid product is isolated from the resulting blend to obtain the intended clathrate compound.

In accordance with the present invention, the guest compound to be combined with (HDPM)$_2$BP for forming the clathrate compound is not specifically limited. Anyone which may form a clathrate compound with (HDPM)$_2$BP may be employed in the present invention. For instance, as one typical example of the microbicides employable in the present invention for the purpose is Cl-MIT. The natural essential oils also employable in the present invention include, for example, cineole, hinoki oil, fragrant olive, jasmine, lemone, quassia oil, cinnamon leaf, menthol, rosemary, palmarosa oil, lavender, spearmint oil, mentha arvensis, etc.

As mentioned in detail in the above, 2,2α-bis(α-hydroxydiphenylmethyl)biphenyl of the present invention is extremely useful as a host molecule to form a clathrate compound with a microbicide or perfume. In addition, the compound is also useful for the purpose of maintaining the effect of perfumes or agricultural chemicals for a long period of time, or is useful as a stabilizer for stabilizing compounds which are unstable to pH variation, heat or ultraviolet rays by converting them into the corresponding clathrate compounds, or is useful for separation, purification or concentration of various compounds by utilizing the selective clathrate compound-producing ability. Further, it is also useful for converting water-soluble microbicides or natural essential oils into powders or for stabilization, concentration, separation or purification of the same. Accordingly, the new compound of the present invention can be utilized in various technical fields.

Specifically, the clathrate compound of the present invention, which comprises (HDPM)$_2$BP as the host compound and a water-soluble microbicide as the guest compound, is usable as a slow-releasing microbicidal agent capable of slowly release the water-soluble microbicide therefrom and has the following advantages:

(1) The durability of the microbicidal activity is long, since the active ingredient gradually dissolves out into water.

(2) As it is solid, it may be shaped into tablets or the like and can be handled with ease.

(3) As the toxicity of the microbicide and the stimulation thereof to the skin may be reduced, the environment in operation with the compound is improved and the safety of the compound is enhanced.

(4) The active ingredient hardly reacts on any other substance so that the microbicidal activity is not lowered.

On the other hand, the clathrate compound of the present invention, which comprises (HDPM)$_2$BP as the host compound and a perfume component of a natural essential oil as the guest compound, is usable as a slow-release perfume and has the following advantages:

(1) As the perfume component gradually gassifies into air, the durability of the perfume effect is long.

(2) As it is solid, it may be handled with ease and it may be shaped also with ease.

(3) Gasification of the perfume component can easily be controlled by varying the grain size of the clathrate compound grains and, as a result, any desired slow-releasability is attainable.

In addition, the host compound of the present invention is also usable for forming a slow-release insecticidal agent containing a natural essential oil as an insecticidal component.

The new host compound of the present invention can easily be prepared by the method of the present invention.

The present invention will be explained in more detail by way of the following examples, which, however, are not intended to restrict the scope of the present invention.

EXAMPLE 1

Production of 2,2'-Bis(α-hydroxydiphenylmethyl)-biphenyl

Reaction Step (1)

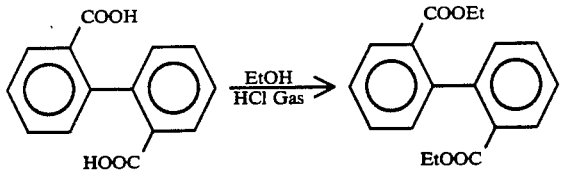

50 g of diphenic acid and 500 ml of ethyl alcohol were added to a one-liter three-neck flask and stirred with a magnetic stirrer to dissolve them. To this was introduced HCl gas with stirring until saturation. After HCl-saturation, HCl gas was further applied to the reaction mixture for 30 minutes. Afterwards, the reaction mixture was heated up to 50° to 60° C. under reduced pressure of 10 to 30 mmHg, whereby the ethanol (EtOH) was concentrated. The residue was dissolved in 500 ml of benzene and then washed with water, saturated sodium bicarbonate solution, water and saturated salt solution in this order The benzene layer was dried with Na$_2$SO$_4$ and then the benzene was removed by distillation. Accordingly, 61 g of diethyl diphenate was obtained. Yield: 99%.

Reaction Step (2)

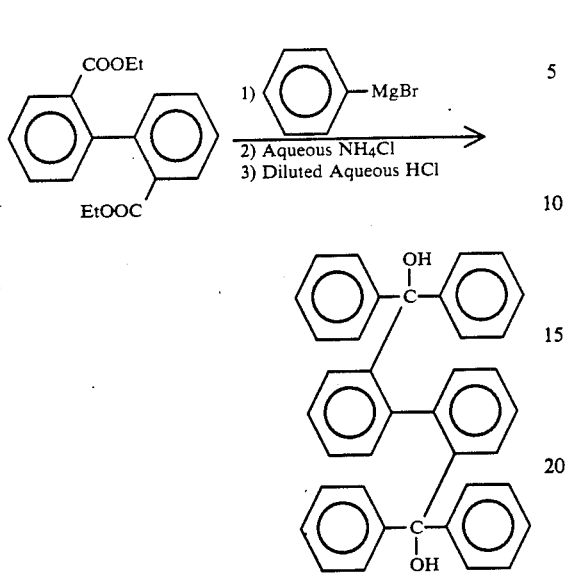

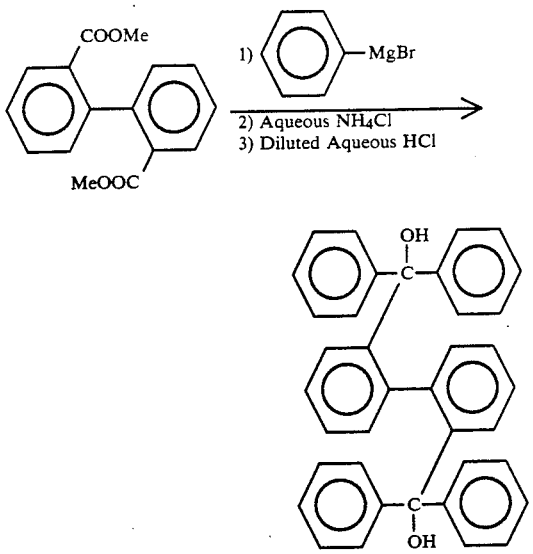

A three-liter three-neck flask was equipped with a CaCl₂ ducthaving cooling means and a dropping funnel. 30 g of Mg was added to the flask, and a dry tetrahydrofuran (THF) was added thereto in an amount of just dipping the magnesium. Next, 10 g of bromobenzene was added thereto with stirring, whereupon the content became hot after initiation of the reaction. Afterwards, a solution prepared by dissolving 184 g of bromobenzene in 500 ml of dry THF was gradually and dropwise added thereto. After completion of the addition, the whole was stirred for further one hour, and then 250 ml of dry THF was added thereto. To this was gradually and dropwise added a solution prepared by dissolving 61 g of the diethyl diphenate prepared in the previous Reaction Step (1) in 500 ml of dry THF. After the addition, the whole was stirred overnight. Afterwards, the reaction mixture was cooled with ice, and 200 ml of saturated aqueous NH₄Cl was gradually added thereto with vigorously stirring. Next, 500 ml of diluted hydrochloric acid was gradually added thereto, and 250 ml of benzene was also added thereto. The oil layer part was isolated and washed with water, saturated sodium bicarbonate solution, water and saturated salt solution in this order. The aqueous layer was extracted with 500 ml of benzene and washed with water, saturated sodium bicarbonate solution, water and saturated salt solution in this order. The benzene extracts were combined and dried with Na₂SO₄, and then the solvent was removed by distillation to obtain a crude (HDPM)₂BP. This was recrystallized from benzene/n-hexane to obtain a clathrate compound of (HDPM)₂BP and benzene. This was further heated at 120° to 140° C. under reduced pressure of 10 to 30 mmHg, whereby the benzene was removed to obtain 75 g of (HDPM)₂BP. Yield: 70%.

The crystal thus obtained had m.p. of 245° to 246° C., and the IR spectrum (nujol method) thereof and the NMR spectrum (solvent: (CDCl₃) are shown in FIG. 1 and FIG. 2, respectively.

EXAMPLE 2

In the same manner as in the Reaction Step (1) in Example 1, except that methyl alcohol was used as the alcohol, dimethyl diphenate was obtained.

50 g of the resulting dimethyl diphenate, 27 g of Mg and 176 g of bromobenzene were used and reacted in the same manner as in the Reaction Step (2) in Example 1. Accordingly, 73 g of (HDPM)2BP was obtained. Yield: 76%.

EXAMPLE 3

Production of (HDPM)₂BP/Cl-MIT Clathrate Compound 2.01 g (3.88×10⁻³ mol) of (HDPM)₂BP and Cl-MIT/MIT mixture containing 1.16 g (7.76×10⁻³ mol) of Cl-MIT were dissolved in 20 ml of chloroform under heat, and the resulting solution was allowed to stand as it was for 48 hours whereupon a white crystal precipitated out. This was filtered under suction to obtain 2.49 g of a crystal. As a result of NMR measurement, the crystal obtained was identified to be (HDPM)₂BR/Cl-MIT clathrate compound where the molar ratio of (HDPM)₂BP/Cl-MIT was 1/1 and the weight ratio of (HDPM)₂BP/Cl-MIT was 77/23.

Dissolution Test of Cl-MIT

Two kinds of (1) (HDPM)₂BP/Cl-MIT clathrate compound obtained above, which was ground and classified through a 42-mesh sieve, and (2) single compound of Cl-MIT were weighed in an amount of 0.23 g as the Cl-MIT content, respectively. Each of them was put in one liter of an ultra-pure water and the proportion of the Cl-MIT content as dissolved out in water after a determined period of time was measured with stirring with a stirrer at 500 rpm The results obtained are shown in Table 1 below.

TABLE 1

| Lapse of Time (day) | Proportion of Dissolution of Cl-MIT (unit: wt. %) | | | | | | | | | |
|---|---|---|---|---|---|---|---|---|---|---|
| | 1 | 3 | 6 | 10 | 14 | 20 | 28 | 38 | 44 | 51 | 64 |
| (1) | 4 | 9 | 14 | 18 | 21 | 25 | 31 | 34 | 38 | 39 | 41 |
| (2) | 100 | 100 | — | — | — | — | — | — | — | — | — |

EXAMPLE 4

Production of (HDPM)$_2$BP/Cineole Clathrate Compound (liquid-liquid reaction)

3.05 g of (HDPM)$_2$BP was dissolved in 20 ml of cineole under heat and allowed to stand as it was for 24 hours, and accordingly a white crystal precipitated out. This was filtered under suction and 3.99 g of a crystal was obtained. As a result of NMR measurement, the crystal was identified to be (HDPM)$_2$BP/cineole clathrate compound where the molar ratio of (HDPM)$_2$BP/cineole was 1/1.2 and the weight ratio of (HDPM)$_2$BP/cineole was 74/26.

Slow-Release Test of Cineole

Two kinds of (1) (HDPM)$_2$BP/cineole clathrate compound obtained above, which was ground and classified through a 42-mesh sieve, and (2) single compound of cineole were weighed in an amount of 0.26 g as the cineole content, respectively. Each of them was put in a laboratory dish having a diameter of 9 cm, and the proportion of the reduced weight of the cineol was measured after a determined period of time under a settled condition. The results obtained are shown in Table 2 below.

TABLE 2

| Proportion of Reduced Weight of Cineole (unit: wt. %) | | | | | | | |
|---|---|---|---|---|---|---|---|
| Lapse of Time (day) | 1/6 | 1 | 8 | 14 | 20 | 26 | 51 |
| (1) | 0.4 | 0.6 | 3.6 | 4.9 | 5.7 | 9.0 | 12.7 |
| (2) | 74.9 | 100 | — | — | — | — | — |

EXAMPLE 5

Production of (HDPM)$_2$BP/Cineole Clathrate Compound (solid-liquid reaction)

2.00 g (3.86×10$^{-3}$ mol) of (HDPM)$^2$BP and 0.60 g (3.90×10$^{-3}$ mol) of cineole were stirred with a spatula for 5 minutes to obtain a solid product. As a result of NMR measurement, the solid product was identified to be (HDPM)$_2$BP/cineole clathrate compound where the molar ratio of (HDPM)2BP/cineole was 1/0.8 and the weight ratio of (HDPM)$_2$BP/cineole was 80/20.

Slow-Release Test of Cineole

Two kinds of (1) (HDPM)$_2$BP/cineole clathrate compound obtained above, which was ground and classified through a 42-mesh sieve, and (2) single compound of cineole were weighed in an amount of 0.20 g as the cineole content, respectively. Each of them was put in a laboratory dish having a diameter of 9 cm, and the proportion of the reduced weight of the cineole was measured after a determined period of time under a settled condition. The results obtained are shown in Table 2 below.

TABLE 3

| Proportion of Reduced Weight of Cineole (unit: wt. %) | | | | | | | |
|---|---|---|---|---|---|---|---|
| Lapse of Time (day) | 1/6 | 1 | 8 | 14 | 20 | 26 | 51 |
| (1) | 1.5 | 4.9 | 22.8 | 31.7 | 42.0 | 49.0 | 72.5 |
| (2) | 74.9 | 100 | — | — | — | — | — |

From the results shown in Table 1 to Table 3 above, it is obvious that the clathrate compounds with (HDPM)$_2$BP as the host compound have an excellent slow-releasability of slowly releasing the guest compound of the microbicide or perfume therefrom.

What is claimed is:

1. A clathrate compound comprising 2,2'-bis(alpha-hydroxydiphenylmethyl)biphenyl as a host compound and an antimicrobial effective amount of 5-chloro-2-methyl-4-isothiazolin-3-one as a guest compound.

2. A clathrate compound as claimed in claim 1, wherein the host compound and the quest compound are mixed in a ratio of 1:1 in a molar ratio.

* * * * *